US00PP12246P2

(12) United States Plant Patent
Vandenberg

(10) Patent No.: US PP12,246 P2
(45) Date of Patent: Dec. 4, 2001

(54) CHRYSANTHEMUM PLANT NAMED 'YELLOW YOKODIAK'

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/525,657

(22) Filed: Mar. 15, 2000

(51) Int. Cl.[7] ..... A01H 5/00
(52) U.S. Cl. ..... Plt./289
(58) Field of Search ..... Plt./289

(56) References Cited

U.S. PATENT DOCUMENTS

P.P. 11,997 * 7/2001 VandenBerg ..... Plt./288
4,616,099 * 10/1986 Sparkes ..... 47/58

OTHER PUBLICATIONS

Shukla, et al., 1993, Mutation studies on early and late varieties of garden chrysanthemum, J. Nuclear Agric. Biol., 22(3–4): 138–142.*
Broertjes, et al., 1980, "A mutant of a mutant of a . . . Irradiation of progressive radiation–induced mutants in a mutation breeding programme with *Chrysanthemum morifolium*", Euphytica, 29: 525–530.*
Gosling, ed., 1979, "The Chrysanthemum Manual—6$^{th}$ edition", The National Chrysanthemum Society, London, Essex Telegraph Press, Ltd., pp. 329–336.*
Broertjes, et al., 1978, "Application of Mutation Breeding Methods in the Improvement of Vegetatively Propagated Crops", Elsevier Sci. Pub. Co., New York, pp. 162–175.*
Searle, et al., 1968, "Chrysanthemums the Year Round", Blanford Press, London, pp. 27–29, 320–327.*
Chan, 1966, "Chrysanthemum and rose mutations induced by x–rays", Am. Soc. Hort. Sci. Proc., pp. 613–620.*
Broertjes, 1966, "Mutation breeding of chrysanthemums", Euphytica, 15: 156–162.*
Dowrick, et al., 1966, "The induction of mutations in chrysanthemum using X– and gamma radiation", Euphytica, 15: 204–210.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Yellow Yokodiak', characterized by its upright, outwardly spreading and uniformly mounded plant habit; freely branching, dense and full plants; dark green foliage; uniform flowering; early flowering, eight-week response time; very large decorative quill-type inflorescences that are about 10.3 cm in diameter; ability to be grown as either a disbudded or centerbudded plants; yellow-colored ray florets; and excellent postproduction longevity with inflorescences and leaves maintaining good substance and color for at least four weeks in an interior environment.

2 Drawing Sheets

BACKGROUND OF THE INVENTION

The present Invention relates to a new and distinct cultivar of Chrysanthemum plant, botanically known as *Dendranthema grandiflora* and hereinafter referred to by the cultivar name Yellow Yokodiak.

The new Chrysanthemum is a product of a mutation induction breeding program conducted by the Inventor in Fort Myers, Fla. and Salinas, Calif. The objective of the program is to create new Chrysanthemum cultivars with desirable inflorescence form and floret colors, good substance, and excellent post-production longevity.

The new Chrysanthemum originated by exposing unrooted cuttings of the Chrysanthemum cultivar Yokodiak, disclosed in U.S. Plant Pat. No. 11,997, to X-ray radiation in September, 1996, in Fort Myers, Fla. Following the radiation treatment, the cuttings were rooted and terminal apices were removed (pinched) three times to promote lateral branch development. After lateral branches from the third pinch reached sufficient size, terminal cuttings were harvested, planted and flowered in a controlled environment in Salinas, Calif. The new Chrysanthemum was discovered and selected by the Inventor as a single flowering plant within this population in April, 1997. The selection of this plant was based on its desirable inflorescence form and ray floret color.

Asexual reproduction of the new Chrysanthemum by terminal cuttings harvested in a controlled environment in Salinas, Calif., has shown that the unique features of this new Chrysanthemum are stable and reproduced true to type in successive generations.

SUMMARY OF THE INVENTION

The cultivar Yellow Yokodiak has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yellow Yokodiak'. These characteristics in combination distinguish 'Yellow Yokodiak' as a new and distinct Chrysanthemum:

1. Upright, outwardly spreading and uniformly mounded plant habit.

2. Freely branching, dense and full plants.

3. Dark green foliage.

4. Uniform flowering.

5. Early flowering, eight-week response time.

6. Very large decorative quill-type inflorescences that are about 10.3 cm in diameter.

7. Ability to be grown as either disbudded or center budded plants.

8. Yellow-colored ray florets.

9. Excellent postproduction longevity with inflorescences and leaves maintaining good substance and color for at least four weeks in an interior environment.

Compared to plants of the parent cultivar, plants of the new Chrysanthemum have yellow-colored ray florets whereas plants of the cultivar Yokodiak have cream to white-colored ray florets.

BRIEF DESCRIPTION OF THE PHOTOGRAPHS

The accompanying colored photographs illustrate the overall appearance of the new Chrysanthemum showng the colors as true as it is reasonably possible to obtain in colored reproductions of this type. Colors in the photographs may differ from the color values cited in the detailed botanical description which more accurately describe the actual colors of the new Chrysanthemum.

The photograph at the top of the first sheet comprises a top perspective view of a typical flowering plant of 'Yellow Yokodiak'.

The photograph at the bottom of the first sheet comprises a close-up view of upper (left) and lower (right) surfaces of typical inflorescences and upper (left) and lower (right) surfaces of typical leaves of the cultivar Yellow Yokodiak.

The photograph at the top of the second sheet comprises a side perspective view of typical flowering plants of 'Yellow Yokodaik' (left) and 'Yokodiak' (right).

The photograph at the bottom of the second sheet comprises a close-up view of typical inflorescences of plants of 'Yellow Yokodiak' (left) and 'Yokodiak'(right).

DETAILED BOTANICAL DESCRIPTION

In the following description, color references are made to The Royal Horticultural Society Colour Chart except where general terms of ordinary dictionary significance are used. The following observations and measurements describe plants grown and flowered during the Autumn in Leamington, Ontario, Canada, under greenhouse conditions which approximate those generally used in commercial potted Chrysanthemum production. Four unrooted cuttings were directly stuck in a 15-cm container and pinched once. Plants used for this description were grown as disbudded-types. Measurements and numerical values represent averages of typical flowering plants.

Botanical classification: *Dendranthema grandiflora* cultivar Yellow Yokodiak.

Commercial classification: Decorative disbudded-type potted Chrysanthemum.

Parentage: Induced mutation of the *Dendranthema grandiflora* cultivar Yokodiak, disclosed in U.S. Plant Pat. No. 11,997.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous decorative potted Chrysanthemum which can be grown as disbudded or center budded plants. Inverted triangle; stems upright and outwardly spreading giving a uniformly mounded appearance to the plant. Freely branching; about three to four lateral branches develop after removal of terminal apex (pinching); dense and full plants.

*Plant height.*—About 28 cm.

*Plant width.*—About 40 cm.

*Stem description.*—Diameter: About 3 mm. Texture: Pubescent. Color: Close to 144A.

*Foliage description.*—Arrangement: Alternate. Length: About 6.8 cm. Width: About 5.4 cm. Apex: Cuspidate. Base: Cuneate to truncate. Margin: Palmately lobed, sinuses between lateral lobes mostly divergent. Texture: Upper and lower surfaces with very fine pubescence; veins prominent on lower surface. Petiole length: About 2 cm. Petiole diameter: About 4 mm. Color: Young foliage upper surface: 147A. Young foliage lower surface: 147B. Mature foliage upper surface: 147A. Mature foliage lower surface: 147B. Venation upper surface: 147A to 147B. Venation lower surface: 147B.

Inflorescence description:

*Appearance.*—Decorative inflorescence form with quill-shaped ray florets. Inflorescences borne on terminals above foliage. Disk and ray florets arranged acropetally on a capitulum.

*Flowering response.*—Under natural conditions, plants flower in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about eight weeks later; early flowering.

*Postproduction longevity.*—Inflorescences and leaves maintain good color and substance for at least four weeks in an interior environment.

*Quantity of inflorescences.*—As a disbudded-type, all lateral inflorescences are removed to allow for maximum terminal inflorescence size. One inflorescence per lateral stem; about three or four inflorescences per plant.

*Inflorescence bud.*—Height: About 8 mm. Diameter: About 9 mm. Color: Close to 143A.

*Inflorescence size.*—Diameter: About 10.3 cm. Depth (height): About 4.3 cm. Diameter of disc: About 2.5 mm, inconspicuous.

*Ray florets.*—Shape: Quill. Orientation: Initially upright, then perpendicular to peduncle. Length: About 5.7 cm. Width: About 5 mm. Apex: Emarginate to acute. Margin: Entire. Texture: Smooth, glabrous, satiny. Number of ray florets per inflorescence: Numerous, about 188. Color: When opening: Tube: Yellow, 7A to 7B. Throat: Yellow, 7A. Fully opened, upper surface: Tube: Yellow, 7A to 7B. Throat: Yellow, 7A.. Fully opened, lower surface: Yellow, 7B to 7C.

*Disc florets.*—Shape: Tubular. Apex: Serrated. Length: About 7 mm. Width: Apex and base, about 1 mm. Number of disc florets per inflorescence: Few, less than 10. Color: Immature: 144A. Mature: Apex: Yellow, 7A. Mid-section: Light green, 145A. Base: White, 155D.

*Reproductive organs.*—Androecium: Present on disc florets only. Anther color: 7A. Pollen amount: None observed. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Yellow Yokodiak', as illustrated and described.

* * * * *

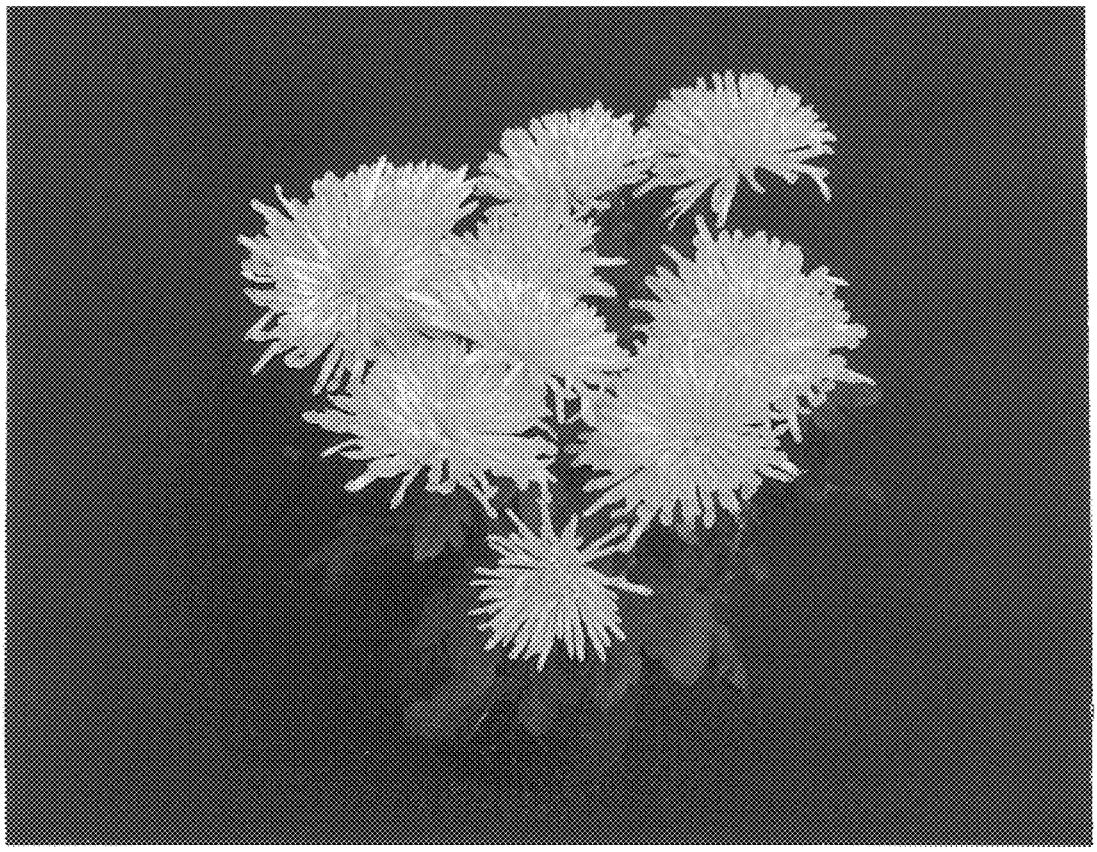
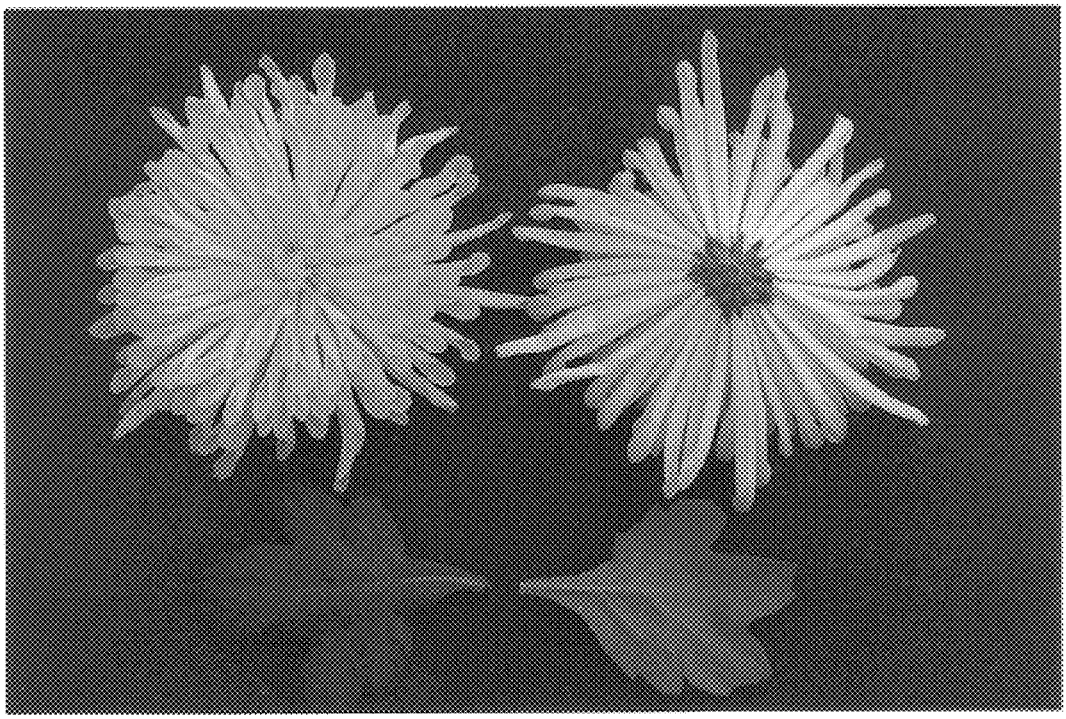

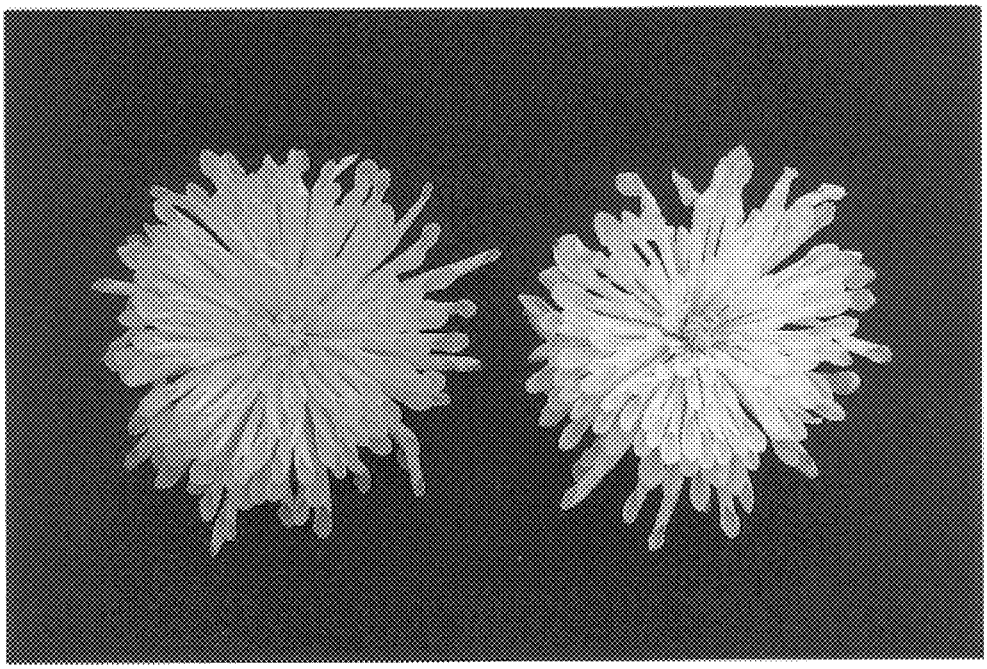

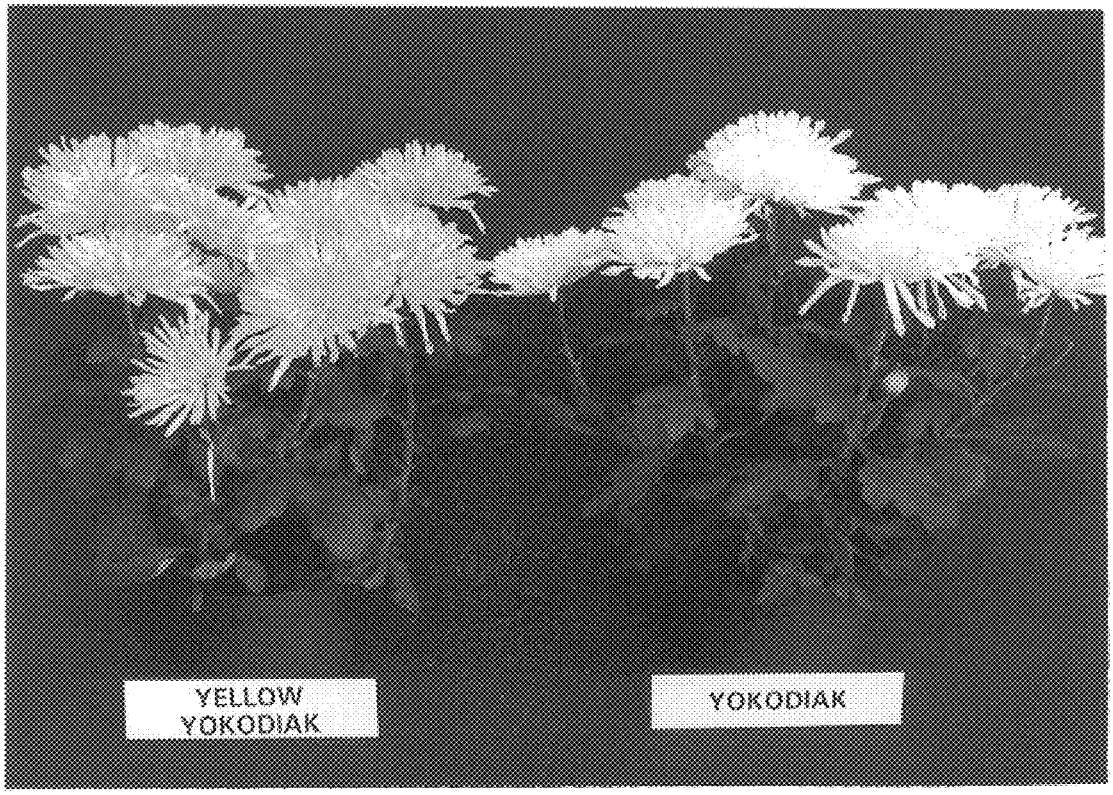
YELLOW
YOKODIAK
YOKODIAK